US00PP25448P3

(12) United States Plant Patent
Geibel

(10) Patent No.: US PP25,448 P3
(45) Date of Patent: Apr. 14, 2015

(54) ***PELARGONIUM* PLANT NAMED 'PACRUBYMEX'**

(50) Latin Name: *Pelargonium peltatum*
Varietal Denomination: Pacrubymex

(71) Applicant: Elsner pac Jungpflanzen, Dresden (DE)

(72) Inventor: Martin Geibel, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 62 days.

(21) Appl. No.: 13/987,052

(22) Filed: Jun. 28, 2013

(65) Prior Publication Data
US 2015/0020265 P1 Jan. 15, 2015

(51) Int. Cl.
*A01H 5/00* (2006.01)

(52) U.S. Cl.
USPC ..... Plt./332

(58) Field of Classification Search
USPC ..... Plt./332
See application file for complete search history.

*Primary Examiner* — Kent L Bell
(74) *Attorney, Agent, or Firm* — The Webb Law Firm

(57) ABSTRACT

A new and distinct flowering *Pelargonium* plant with big, bi-colored flowers and strong vigor.

1 Drawing Sheet

Botanical classification: *Pelargonium peltatum.*
Varietal denomination: 'Pacrubymex'.

BACKGROUND OF THE INVENTION

The present invention comprises a new and distinct cultivar of *Pelargonium peltatum* known by the varietal name 'Pacrubymex'. The new variety was discovered in a planned breeding program in Dresden, Germany in the summer of 2009. The purpose of the breeding program was to develop bi-colored, semi-double flowering Ivy *Pelargoniums* (geraniums) with a stable flower pattern. The new variety is the result of a crossing a bulk of different genotypes to obtain big, double flowers with a red color and good heat resistance. Cuttings from the seedling with the best flowering characteristics and best growth habit were grafted on 'Pacshim' (U.S. Plant Pat. No. 20,975) to transfer the pattern of bi-colored stripes. When the grafted tips that flowered were also bi-colored, cuttings were made and plants of the resulting striped new variety were tested over three years. The most stable plant was chosen and named 'Pacrubymex'. The new variety is similar to 'Pacruby' (U.S. Plant Pat. No. 21,868) in trailing habit, leaf size and color, and all over season flowering. The new variety is less vigorous than 'Pacruby'. 'Pacrubymex' has red-white (43A and 36D) colored petals, while 'Pacruby' only exhibits red (45A) colored petals. The new variety was first asexually reproduced in November of 2009 by cuttings in Dresden, Germany. The new variety has been trial and field tested in Dresden and has been found to retain its distinctive characteristics and remain true to type through successive propagations.

The following characteristics further distinguish the new variety from other *Pelargonium* varieties known to the breeder:

Stable, bi-colored flowers;
Big, double flowers;
Strong vigor;
Good trailing habit;

All over season flowering; and
Good heat stability.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions and carried out in a greenhouse in Dresden, Germany. The new variety was grown in a 19 cm. pot, with treatment of Cycocel® 720 0.2% four times, and two pinchings. The readings and measurements were taken on a 9-month old plant in a room without direct sunlight or artificial light. Color references are primarily to The 1995 edition of The R.H.S. Colour Chart of The Royal Horticultural Society of London.

PLANT

Time to initiate roots (days, temperature): About 21 days at about 18-20° C.
Time to develop roots (days, temperature): About 28 days at about 18-20° C.
Time to produce a finished flowering plant from a rooted cutting: About 12 weeks in a 12 cm container.
Type: Ivy.
Rooting habit: Freely branching roots.
Form: Trailing.
Height from media surface to top of foliage: 25 cm.
Height from media surface to top of flowers: 30 cm.
Plant diameter: 50 cm.
Vigor: Vigorous.
Strength (need for artificial support): Long branches need support in production.
Branching habit: Freely branching.

Stem:
*Main stem length.*—30-50 cm.
*Diameter.*—5 mm.
*Color.*—Close to 144A.
*Texture.*—Slightly rough.
*Pubescence.*—Light.
*Internode length.*—2-3 cm.
Lateral branches:
*Length.*—Primary: 20-40 cm.
*Secondary.*—2-25 cm.
*Diameter.*—Primary: 4 mm.
*Secondary.*—3 mm.
*Internode length.*—2-3 cm.
*Texture.*—Slightly rough.
*Pubescence.*—Light.
*Color.*—144A.
Foliage:
*Arrangement.*—Mainly opposite, sometimes alternate.
*Stipules.*—Size: Length: 11 mm. Width: 7 mm.
*Color.*—147A.
Zone:
*Location.*—2 cm from margin.
*Color.*—200A on young leaves, but is lost after maturity.
Size of leaf:
*Length.*—3.5 cm.
*Width.*—6 cm.
Shape of leaf (generally): Ivy shaped.
Shape of apex: Cuneate.
Shape of base: Open.
Texture: Leathery.
Aspect: Glossy.
Margin type: Lobed, significantly undulated.
Pubescence:
*Upper surface.*—Glabrous.
*Lower surface.*—Glabrous.
Color:
*Young leaves.*—Upper surface: Close to 137A. Lower surface: Close to 137C.
*Mature leaves.*—Upper surface: Close to 137A. Lower surface: Close to 137C.
Petiole:
*Length.*—20 mm.
*Diameter.*—2 mm.
*Color.*—146A.
Veins:
*Venation type.*—Palmate.
*Color.*—Upper surface: Close to 144A. Lower surface: Close to 144A.

INFLORESCENCE

Bud:
*Stage of development when bud characteristics determined.*—Before color appears.
*Shape of cluster.*—Like a bell.
*Diameter of cluster.*—2.5 cm.
*Number of buds per cluster.*—6.
*Shape of individual bud.*—Spindle-shaped.
*Length of individual bud.*—13 mm.
*Width of individual bud.*—5 mm.
Natural flowering season: Spring until frost in moderate climates.
Blooming habit: Continuous, with early blooming.
Umbel diameter: 9 cm.
Umbel depth: 6 cm.
Borne: Umbel, flowers on pedicel, pedicel on peduncle.
Inflorescence position: Above foliage.
Number of inflorescences per lateral branch: About 3 at the same time.
Lastingness of an individual flower: 6-10 days.
Florets:
*Form.*—Flat.
*Number per umbel.*—6.
*Diameter.*—55 mm.
*Depth.*—20 mm.
Petals:
*Color.*—Upper surface: Margin and stripes are 43A, fading to white in between. Lower surface: White with a margin of 50A, more or less no stripes present.
*Shape.*—Obovate.
*Length.*—30 mm.
*Width.*—18 mm.
*Apex shape.*—Round.
*Base shape.*—Attenuate.
*Margin.*—Entire and undulated.
*Number per floret.*—11.
*Texture.*—Smooth, glabrous, and velvety.
*Tonality from a distance.*—Bi-colored red/white.
Petaloids:
*Quantity.*—3-8.
*Shape.*—Irregular.
*Color (upper and lower surface).*—Margin and stripes are 43A, fading to white in between.
*Length.*—5-15 mm.
*Width.*—3-10 mm.
Pedicel:
*Length.*—25 mm.
*Diameter.*—2 mm.
*Color.*—144A.
Peduncle:
*Length.*—9-14 cm.
*Diameter.*—3 mm.
*Texture.*—Sticky and glabrous.
*Color.*—144A.
Fragrance: None.
Disease resistance: Unknown.
Temperature tolerance: Good heat stability.
Drought tolerance: Medium.

REPRODUCTIVE ORGANS

Stamens:
*Number (per flower).*—10-15.
*Filament.*—Length: 8 mm. Color: White.
*Anthers.*—Shape: Elongated; short tube. Length: 2 mm. Color: 79A.
Pollen:
*Color.*—169D.
*Amount.*—Much.
Pistils:
*Number.*—1.
*Length.*—10 mm.
Style:
*Length.*—3 mm.
*Color.*—White.
Stigma:
*Shape.*—Actinomorphic, 5-6 parted.
*Color.*—64A.
*Size.*—4 mm.

Ovaries:

*Texture*.—Pubescence present.
*Length*.—5 mm.
*Width*.—2 mm.
*Color*.—148D.

I claim:

1. A new and distinct variety of *Pelargonium* plant substantially as shown and described.

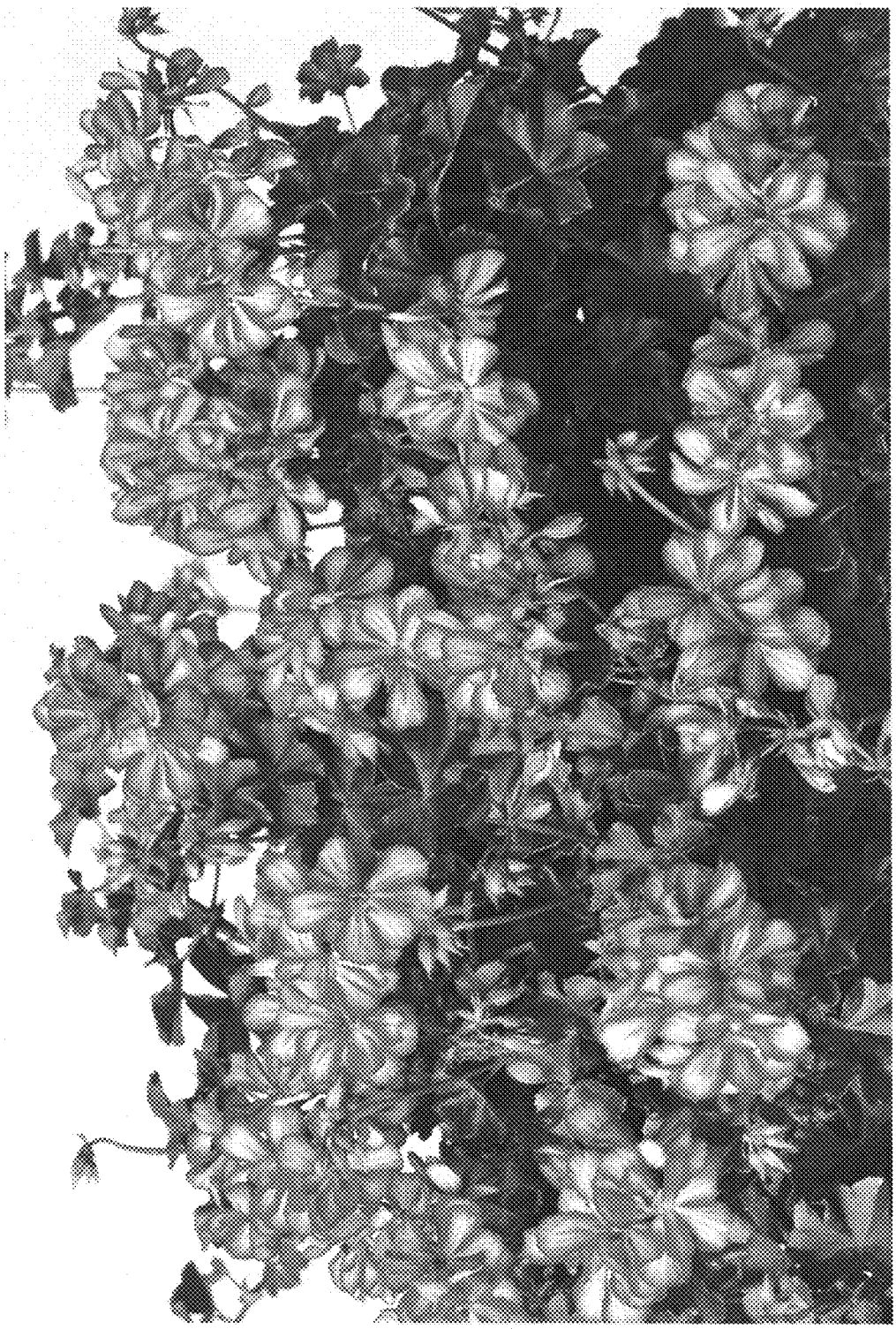

* * * * *